US010679733B2

(12) United States Patent
Botea et al.

(10) Patent No.: US 10,679,733 B2
(45) Date of Patent: Jun. 9, 2020

(54) EFFICIENT RETROSYNTHESIS ANALYSIS

(71) Applicant: International Business Machines Corporation, Armonk, NY (US)

(72) Inventors: Adi I. Botea, Dublin (IE); Beat Buesser, Dublin (IE); Bei Chen, Dublin (IE); Akihiro Kishimoto, Dublin (IE); John Savage, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 85 days.

(21) Appl. No.: 15/286,972

(22) Filed: Oct. 6, 2016

(65) Prior Publication Data
US 2018/0101663 A1    Apr. 12, 2018

(51) Int. Cl.
G05B 21/00        (2006.01)
G16C 20/10        (2019.01)
G16C 20/90        (2019.01)

(52) U.S. Cl.
CPC ............. *G16C 20/10* (2019.02); *G16C 20/90* (2019.02)

(58) Field of Classification Search
USPC ............................................ 702/19; 700/266
See application file for complete search history.

(56) References Cited

U.S. PATENT DOCUMENTS

2004/0153250 A1    8/2004    Hurst et al.
2005/0177280 A1    8/2005    Almstetter et al.

FOREIGN PATENT DOCUMENTS

WO        2005054978 A2        6/2005

*Primary Examiner* — Lam S Nguyen
(74) *Attorney, Agent, or Firm* — Cantor Colburn LLP; Kurt Goudy

(57) ABSTRACT

Techniques for efficient retrosynthesis analysis are provided. A computer-implemented method for determining whether a target compound can be synthesized using known pathways for similar compounds includes receiving, by a processor, target compound data including a target compound. The method further includes obtaining, by the processor, a similar compound to the target compound, along with a reaction rule for synthesizing the similar compound. The method further includes applying, by the processor, the reaction rule to the target compound to generate a set of precursors. The method further includes generating, by the processor, a notification based on the set of precursors.

20 Claims, 5 Drawing Sheets

EFFICIENT RETROSYNTHESIS ANALYSIS

BACKGROUND

The present invention relates in general to discovering pathways for chemical compound synthesis. More specifically, the present invention relates to an efficient retrosynthesis analysis system and computer-implemented method for determining whether a target compound can be synthesized using known pathways for similar compounds.

Discovering pathways to create new chemical compounds plays an important role in the pharmaceutical, chemical, food, material and other industries. These pathways are conventionally discovered manually by chemists using techniques such as retrosynthetic analysis. Retrosynthetic analysis involves the transformation of a target compound into progressively simpler or commercially available precursor compounds without any assumptions regarding starting materials. Intermediate precursors known for synthesizing the target compound are initially selected and are themselves progressively transformed into even simpler precursor compounds until only simple or commercially available compounds are required. The goal of retrosynthetic analysis is the structural simplification of the target compound and the discovery of synthetic routes for synthesizing the target compound.

SUMMARY

According to embodiments of the present invention, a computer-implemented method for determining whether a target compound can be synthesized using known pathways for similar compounds is provided. The computer-implemented method includes receiving, by a processor, target compound data including a target compound. The method further includes obtaining, by the processor, a similar compound to the target compound, along with a reaction rule for synthesizing the similar compound. The method further includes applying, by the processor, the reaction rule to the target compound to generate a set of precursors. The method further includes generating, by the processor, a notification based on the set of precursors.

According to embodiments of the present invention, a system for determining whether a target compound can be synthesized using known pathways for similar compounds is provided. The system includes a memory having computer readable instructions and a processing device for executing the computer readable instructions. The computer readable instructions cause the processing device to receive target compound data including a target compound and to obtain a similar compound to the target compound. The computer readable instructions further causes the processing device to obtain a reaction rule for synthesizing the similar compound, to apply the reaction rule to the target compound to generate a set of precursors, and to generate a notification based on the set of precursors.

According to embodiments of the present invention, a computer program product for determining whether a target compound can be synthesized using known pathways for similar compounds is provided. The computer program product includes a computer readable storage medium having program instructions embodied therewith, the program instructions executable by a processing device to cause the processing device to perform a method. The method can include receiving target compound data including a target compound. The method further includes obtaining a similar compound to the target compound along with a reaction rule for synthesizing the similar compound. The method further includes applying the reaction rule to the target compound to generate a set of precursors. The method further includes generating a notification based on the set of precursors.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Figure 1:
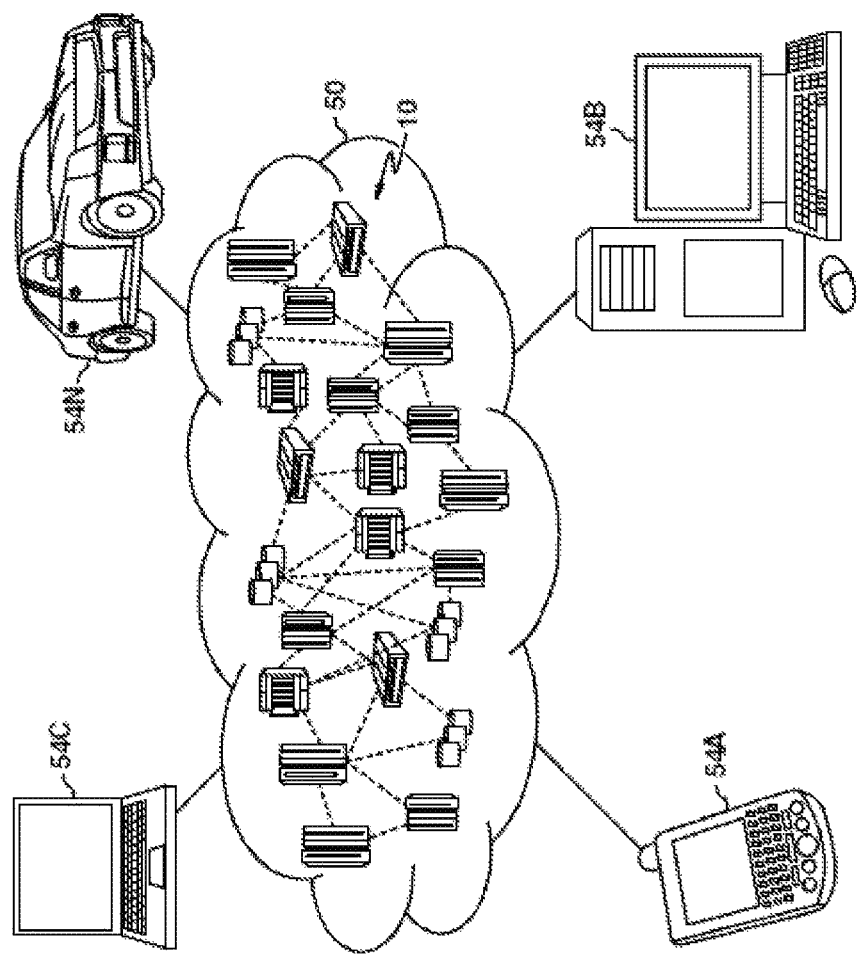
FIG. 1 depicts a cloud computing environment according to an embodiment of the present invention.

In accordance with one or more embodiments of the invention, efficient retrosynthesis analysis systems, methods, and computer program products for determining whether a target compound can be synthesized using known pathways for similar compounds are provided. Various embodiments of the present invention are described herein with reference to the related drawings. Alternative embodiments can be devised without departing from the scope of this invention. References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

Additionally, the term "similar compound" is used herein to mean a compound having a similarity score (e.g., a Jaccard coefficient) with respect to a target compound that satisfies a similarity threshold (e.g., a value greater than or equal to 0.90) as is discussed in further detail herein.

For the sake of brevity, conventional techniques related to computer processing systems and abstraction models may or may not be described in detail herein. Moreover, it is understood that the various tasks and process steps described herein can be incorporated into a more comprehensive procedure, process or system having additional steps or functionality not described in detail herein.

Turning now to a detailed description of the present invention, as previously noted herein, discovering pathways to create new chemical molecules or compounds plays an important role in various industries and these pathways are conventionally discovered manually by chemists using techniques such as retrosynthetic analysis. This interest in discovering new pathways is based in part on a multi-industry need for designing compounds with simpler structures to facilitate easier or cheaper synthesis. In the pharmaceutical industry, for example, drug molecules usually consist of active sites and support structures. The support structures can be replaced with simpler structures without affecting the active sites and final drug efficacy by discovering new pathways to synthesize these simpler structures. Manually discovering these pathways is highly laborious and subject to human error. Moreover, manual retrosynthetic analysis often results in suboptimal pathways having a low success rate (i.e., a success rate for synthesizing a target compound of less than one percent). Computer software for automating the discovery of these pathways is not widely adopted because of high computational costs which often fail to find successful pathways. In particular, a conventional automated retrosynthesis approach requires exhaustively searching all reaction rules which can be used to synthesize a target compound. For each reaction rule a set of precursor compounds are identified, each requiring an exhaustive search until a pathway requiring only simple starting materials is discovered. A complication of this approach arises from the fact that the number of available compounds is ever increasing. For example, the National Center of Biotechnology Information (NCBI) PubChem database now contains more than 30 million molecules. As the quantity of known compounds (i.e., the chemical space) is increasing, the computational overhead required for brute force exhaustive searches is increasing, resulting in a substantial reduction in search efficiency and a substantial increase in search cost. Thus, efficient retrosynthesis analysis systems, methods, and computer program products for determining whether a target compound can be synthesized using known pathways for similar compounds are desired.

One or more embodiments provide an efficient retrosynthesis analysis system, a computer-implemented method, and a computer product for determining whether a target compound can be synthesized using known pathways for similar compounds. The system identifies similar compounds to the target compound whose synthesis pathways are already known from either the baseline knowledge of the art or from previous pathways for prior target compounds stored in the system for reuse according to one or more embodiments. Target compound similarity is determined using known techniques, such as Jaccard similarity (also known as Tanimoto similarity), ALOGP, and autocorrelation polarizability. The system then checks whether the target compound can be synthesized in a similar way as one or more of the similar compounds, e.g., using a reaction rule. A reaction rule expresses the generation of a compound from precursors. If synthesis is possible using a particular reaction rule, the system applies the reaction rule to generate precursors for the target compound. The system then determines whether the precursors themselves have known synthesis pathways. Precursors having known pathways can be referred to herein as "starting materials." For any precursors which do not have known synthesis pathways the system repeats the process (i.e., as was applied to the target compound) to generate similar compounds for those precursors. In this manner, only reaction rules corresponding to similar compounds are applied by the system. The process continues until a pathway for synthesizing the target compound is discovered that only requires precursors which can themselves be generated using known pathways (i.e., synthesizing the target compound only requires starting materials). As the system does not require an exhaustive search of all possible reaction rules which can be used to synthesize the target compound the search space required for retrosynthesis analysis is drastically reduced.

One or more embodiments of the invention include or yield various technical features, technical effects, and/or improvements to technology. Example embodiments of the invention provide an efficient retrosynthesis analysis system configured to perform an automatic, unsupervised process to determining whether a target compound can be synthesized using known pathways for similar compounds by receiving target compound data including a target compound; obtaining a similar compound to the target compound; obtaining a reaction rule for synthesizing the similar compound; applying the reaction rule to the target compound to generate a set of precursors; and generating a notification based on the set of precursors. These aspects of the invention constitute technical features that yield the technical effect of discovering synthesis pathways via an efficient retrosynthesis analysis process that avoids the need for manually performing a retrosynthesis analysis and the technical effect of using a machine learning technique to progressively improve pathway discovery by identifying and storing discovered pathways for future use. As a result of these technical features and technical effects, an efficient retrosynthesis analysis system in accordance with embodiments of the present invention represents an improvement to existing retrosynthetic analysis techniques. It should be appreciated that the above examples of technical features, technical effects, and improvements to technology are merely illustrative embodiments of the invention and are not exhaustive.

An efficient retrosynthesis analysis system, a computer-implemented method, and a computer product for determining whether a target compound can be synthesized using known pathways for similar compounds in accordance with one or more embodiments of the present invention are described in detail below by referring to the accompanying drawings in FIGS. 1-5.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 for determining whether a target compound can be synthesized using known pathways for similar compounds is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Cloud computing nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
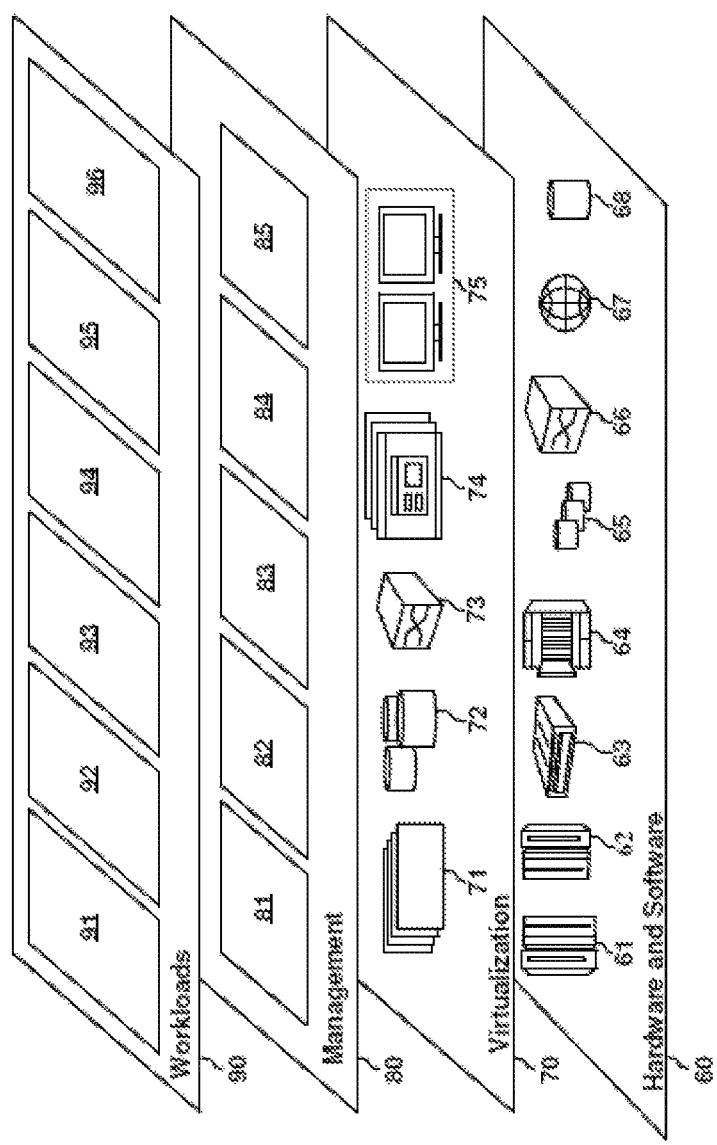
FIG. 2 depicts abstraction model layers according to an embodiment of the present invention.

Referring now to FIG. 2, a set of functional abstraction layers provided by cloud computing environment 50 (FIG. 1) is shown. It is understood that the components, layers, and functions shown in FIG. 2 are intended to be illustrative only and that embodiments of the invention are not limited thereto. As illustrated, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In some embodiments, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Figure 4:
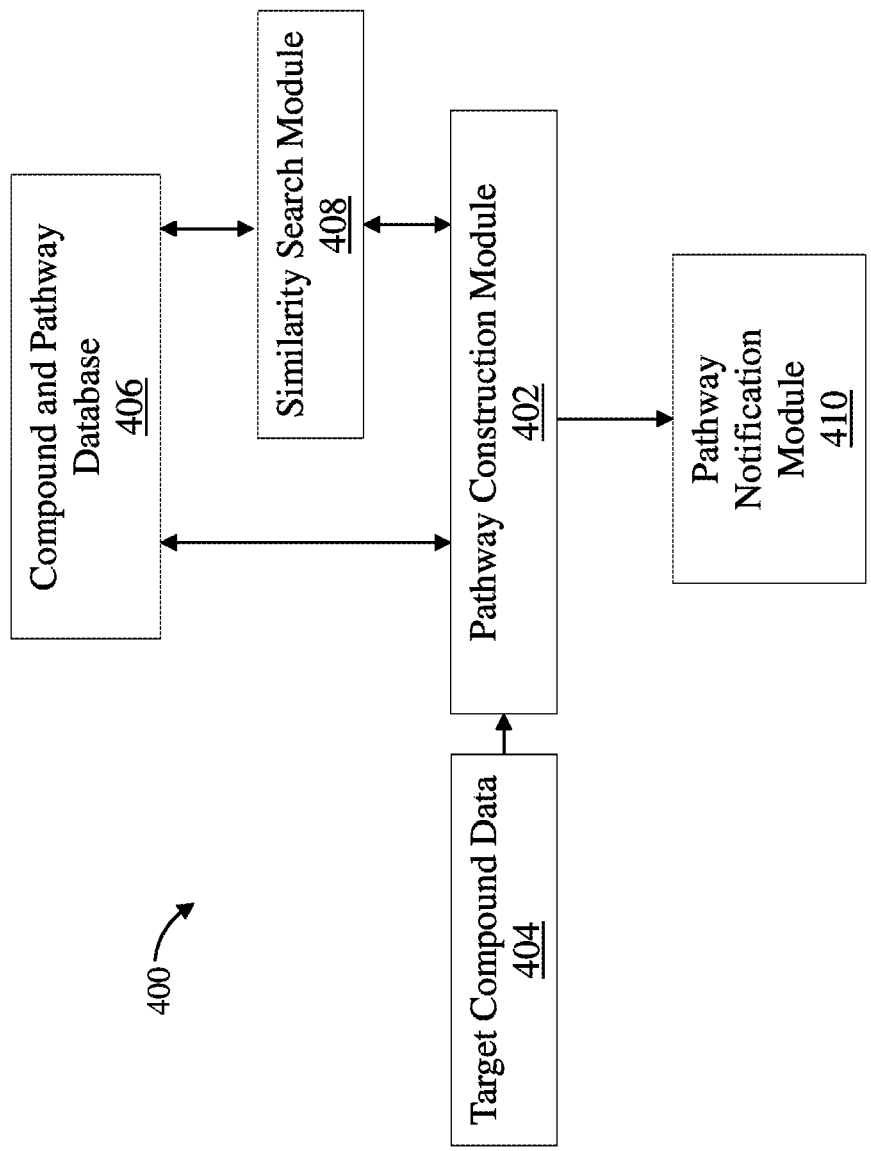
FIG. 4 depicts a block diagram of a processing system for determining whether a target compound can be synthesized using known pathways for similar compounds according to one or more embodiments of the present invention.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and retrosynthesis analysis container 96. In some embodiments, retrosynthesis analysis container 96 provides the functionality of the pathway construction module 402 and the similarity search module 408 (as depicted in FIG. 4).

Figure 3:
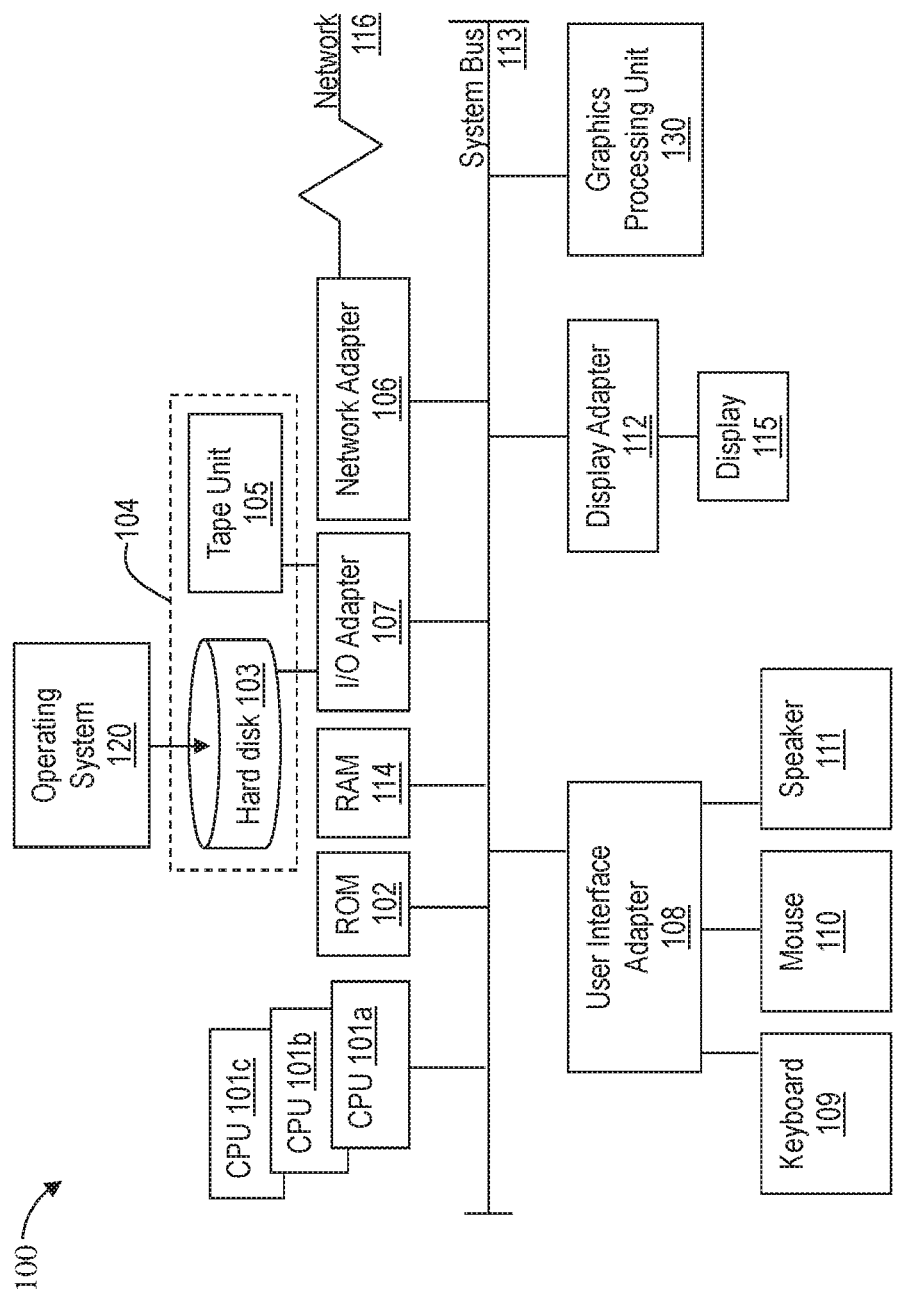
FIG. 3 depicts a block diagram of a processing system for determining whether a target compound can be synthesized using known pathways for similar compounds according to one or more embodiments of the present invention.

FIG. 3 illustrates a block diagram of a processing system 100 for providing efficient retrosynthesis analysis according to one or more embodiments. Processing system 100 can have one or more central processing units (processors) 101*a*, 101*b*, 101*c*, etc. (collectively or generically referred to as processor(s) 101 and/or as processing device(s) 101). In some embodiments, each processor 101 can include a reduced instruction set computer (RISC) microprocessor. Processors 101 are coupled to system memory (e.g., random access memory (RAM) 114) and various other components via a system bus 113. Read only memory (ROM) 102 is coupled to system bus 113 and can include a basic input/output system (BIOS), which controls certain basic functions of processing system 100.

Further illustrated are an input/output (I/O) adapter 107 and a network adapter 106 coupled to system bus 113. I/O adapter 107 can be a small computer system interface (SCSI) adapter that communicates with a hard disk 103, a tape unit 105, or any other similar component. I/O adapter 107, hard disk 103, and tape unit 105 are collectively referred to herein as mass storage 104. Operating system 120 for execution on processing system 100 can be stored in mass storage 104. A network adapter 106 interconnects system bus 113 with an outside network 116 enabling processing system 100 to communicate with other such systems.

A display (e.g., a display monitor) 115 is connected to system bus 113 by display adaptor 112, which can include a graphics adapter to improve the performance of graphics intensive applications and a video controller. In some embodiments, adapters 106, 107, and/or 112 can be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 can be interconnected to system bus 113 via user interface adapter 108, which can include, for example, a Super I/O chip integrating multiple device adapters into a single integrated circuit.

In some embodiments, processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured herein, processing system 100 includes processing capability in the form of processors 101, storage capability including system memory (e.g., RAM 114), and mass storage 104, input means such as keyboard 109 and mouse 110, and output capability including speaker 111 and display 115. In some aspects of the present invention, a portion of system memory (e.g., RAM 114) and mass storage 104 collectively store an operating system such as the AIX® operating system from IBM Corporation to coordinate the functions of the various components shown in processing system 100.

FIG. 4 illustrates a block diagram of a processing system 400 for determining whether a target compound can be synthesized using known pathways for similar compounds according to one or more embodiments. The various components, modules, engines, etc. described regarding FIG. 4 can be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these. In some embodiments, the engine(s) described herein can be a combination of hardware and programming. The programming can be processor executable instructions stored on a tangible memory, and the hardware can include processor 101 (FIG. 3) for executing those instructions. Thus a system memory can store program instructions that when executed by processor 101 implement the engines described herein. Other engines can also be utilized to include other features and functionality described in other examples herein.

Processing system 400 can include processor 101, pathway construction module 402, target compound data 404, compound and pathway database 406, similarity search module 408, and notification module 410. Compound and pathway database 406 can include a single database or one or more databases. In some embodiments, the compound and pathway database 406 includes separate compound databases and pathway databases. Alternatively or additionally, the processing system 400 can include dedicated hardware, such as one or more integrated circuits, Application Specific Integrated Circuits (ASICs), Application Specific Special Processors (ASSPs), Field Programmable Gate Arrays (FPGAs), or any combination of the foregoing examples of dedicated hardware, for performing the techniques described herein.

Pathway construction module 402 receives target compound data 404 as input from a client (e.g., as input from a user of the processing system 400 or as input from another system) according to one or more embodiments. The target compound data 404 includes a compound name, a chemical structure, and/or a molecular fingerprint for identifying a target compound. A molecular fingerprint, for example, can be represented by bit strings that summarize molecular information such as the presence or absence of particular functional groups or combinatorial features.

In some embodiments, pathway construction module 402 uses a similarity function to calculate a similarity score between the target compound data 404 and one or more compounds in the compound and pathway database 406 to generate a set of similar compounds whose synthesis pathways are already known. In some embodiments, the pathway construction module 402 sends a request to a similarity search module 408 that applies one or more similarity functions to one or more compounds in the compound and pathway database 406. The similarity search module 408 returns to the pathway construction module 402 a set of similar compounds, each having a sufficient similarity score. In some embodiments, the pathway construction module 402 sends the request for similar compounds responsive to receiving the target compound data 404. The similar compound synthesis pathways can be stored in the compound and pathway database 406. In some embodiments, the compound and pathway database 406 is populated with known compounds having known properties (e.g., known chemical structures and/or molecular fingerprints) and known synthesis pathways. In some embodiments, the compound and pathway database 406 includes partial pathways for one or more compounds. In some embodiments, a discovered pathway for a target compound is stored for reuse in the compound and pathway database 406. In this manner, the compound and pathway database 406 is progressively improved over time.

The similarity functions utilized by the pathway construction module 402 and the similarity search module 408 include any known techniques or chemoinformatics for generating similar compounds to a target compound, such as, for example, Jaccard similarity (also known as Jaccard index or Tanimoto similarity), ALOGP, autocorrelation polarizability, or combinations thereof. In some embodiments, the pathway construction module 402 and the similarity search module 408 filter the complete list of compounds stored in the compound and pathway database 406 using known techniques for efficient searching, such as, for example, succinct multibit tree searching or succinct interval-splitting tree algorithm (SITA) searching. In this manner, Jaccard similarities are only calculated for a subset of the compounds stored in the compound and pathway database 406.

In some embodiments, a compound is considered sufficiently similar to a target compound if a similarity score (e.g., a Jaccard coefficient) for the compound with respect to the target compound is greater than a threshold of about 0.85, or about 0.90. In some embodiments, the similarity score threshold can be adjusted to relax or tighten the similarity functions. For example, the threshold can be increased to about 0.90, or to about 0.95, to tighten the similarity functions. Doing so would increase the level of similarity (as defined in this example by Jaccard similarity) that a particular compound must achieve to be included in the set of similar compounds, resulting in fewer similar compounds and a set of similar compounds having a relatively higher average similarity with respect to the target compound. Conversely, the threshold can be decreased to increase the number of compounds in the set of similar compounds.

The pathway construction module 402 receives the set of similar compounds and determines, for each compound in the set of similar compounds, a reaction rule for synthesizing the compound. The pathway construction module 402 then determines whether the reaction rule is valid for the target compound (i.e., whether the reaction rule results in a valid pathway for synthesizing the target compound). If synthesis of the target compound is possible using the reaction rule, the pathway construction module 402 applies the reaction rule to the target compound to generate precursors. In this manner, the pathway construction module 402 avoids an exhaustive search of the entire space of all available reaction rules. In some embodiments, the reaction rules are not instantiated (i.e., the reaction rule generates different precursors when applied to the target compound than are generated when the same reaction rule is applied to the similar compound).

The pathway construction module 402 then searches the compound and pathway database 406 to determine whether all of the precursors are starting materials. Starting materials are those compounds which are stored in the compound and pathway database 406 as commercially available compounds or as compounds having known synthesis pathways. The pathway construction module 402 generates a set of similar compounds and corresponding precursor reaction rules for each precursor which is not a starting material, in a like manner as was initially done for the target compound. In effect, each precursor which is not a starting material serves as a new target compound for a new similarity function. The precursor reaction rules are applied to the precursors to generate additional precursors. Consequently, the cycle of identifying a similar compound for a target compound having an unknown or partially unknown synthesis and applying a valid reaction rule of the similar compound to the target compound to generate precursors is repeated until a complete pathway (i.e., series of reaction rules) is discovered for the target compound. A complete pathway is a synthesis pathway that requires only starting materials. Once a complete pathway is discovered, the pathway notification module 410 receives the complete pathway from the pathway construction module 402. The pathway notification module 410 outputs a notification including the complete pathway to the client. In some embodiments, the pathway notification module 410 outputs the notification to a user device, such as, for example, a display, a phone, a computer, or a television. In some embodiments, the pathway notification module 410 outputs the notification to a client system (e.g., a chemoinformatics software or service).

In some embodiments, the pathway construction module 402 is unable to discover valid reaction rules for the target compound and a failed result is stored in the compound and pathway database 406. In some embodiments, the pathway notification module 410 outputs a failure notification. In some embodiments, the pathway construction module 402 can efficiently determine that a complete pathway is infeasible. For example, the similarity search module 408 can return a similar compound which is known to be infeasible to synthesize. In some embodiments, the pathway notification module 410 outputs a notification that the target compound is similar to a compound which is infeasible to synthesize. In some embodiments, compounds proven to be feasible or infeasible to synthesize are stored in the compound and pathway database 406. In some embodiments, the pathway construction module 402 does not determine reaction rules for a similar compound, regardless of similarity score, unless the compound is known to be feasible to synthesize.

In some embodiments, features of the pathway construction module 402 and similarity search module 408 can be included as an enhancement package or "special" search within existing commercial chemoinformatics software and services, e.g., ARChem Route Designer. In some embodiments, an initial conventional retrosynthetic analysis (i.e., a "normal" search) is performed to try to discover a pathway having only starting materials. If the "normal" search instead identifies a compound with an unknown or partially unknown synthesis pathway a "special" search is performed to try to efficiently generate the pathway. In some embodiments, the "special" search is performed according to one or more embodiments to discover a complete pathway for the compound and the pathway notification module 410 provides the complete pathway as output to the chemoinformatics software. In some embodiments, the "special" search is unable to discover valid reaction rules for the compound and the failed result is stored in the compound and pathway database 406. In this case the "normal" search can be exhaustively used to verify the existence of a pathway for the compound. In this manner, the chemoinformatics software relies on the "special" search to efficiently discover a pathway for a compound having an unknown or partially unknown pathway and on the "normal" search for pathways requiring only starting materials or when the "special" search fails and an exhaustive search is required. Consequently, the overhead of the "special" search within the chemoinformatics software is small and the search space which would normally be exhaustively searched (i.e., by a pure "normal" search) is drastically reduced.

Moreover, as the number of reaction rules and possible precursors increases the advantageous reduction in search space increases. For example, the "special" search, assuming b reaction rules, each of which generates p precursors, requires a search space of $O(p^d)$, where d is the number of layers in the search space (a first "layer" being a set of compounds, such as, for example, the target compound and a second "layer" being a set of precursors for the first layer. This is theoretically the minimum effort to discover a pathway. By comparison, the "normal" search space is $O(b^d p^d)$.

Algorithm Pseudo-Code

In some embodiments, features of the pathway construction module 402 and similarity search module 408 can be included in chemoinformatics systems as an algorithm (e.g., Algorithm Search(x)) having the following pseudo-code:

```
Require: compound s
1:  if s is a start material then
2:    return true
3:  calculate a set CS of compounds similar to s
4:  set of reaction rules R = φ
5:  for each c ∈ CS do
6:    r = extract final reaction step to synthesize c
7:    if r is applicable to s then
8:      R = R ∪ {r}
9:  for each r ∈ R do
10:   calculate a set SPC of precursors obtained by s and r
11:   result = true
12:   for each precursor p ∈ SPC do
13:     result = Search(p)
14:     if result == false then
15:       break
16:   if result == true then
17:     return true
18:   return false
```

Figure 5:
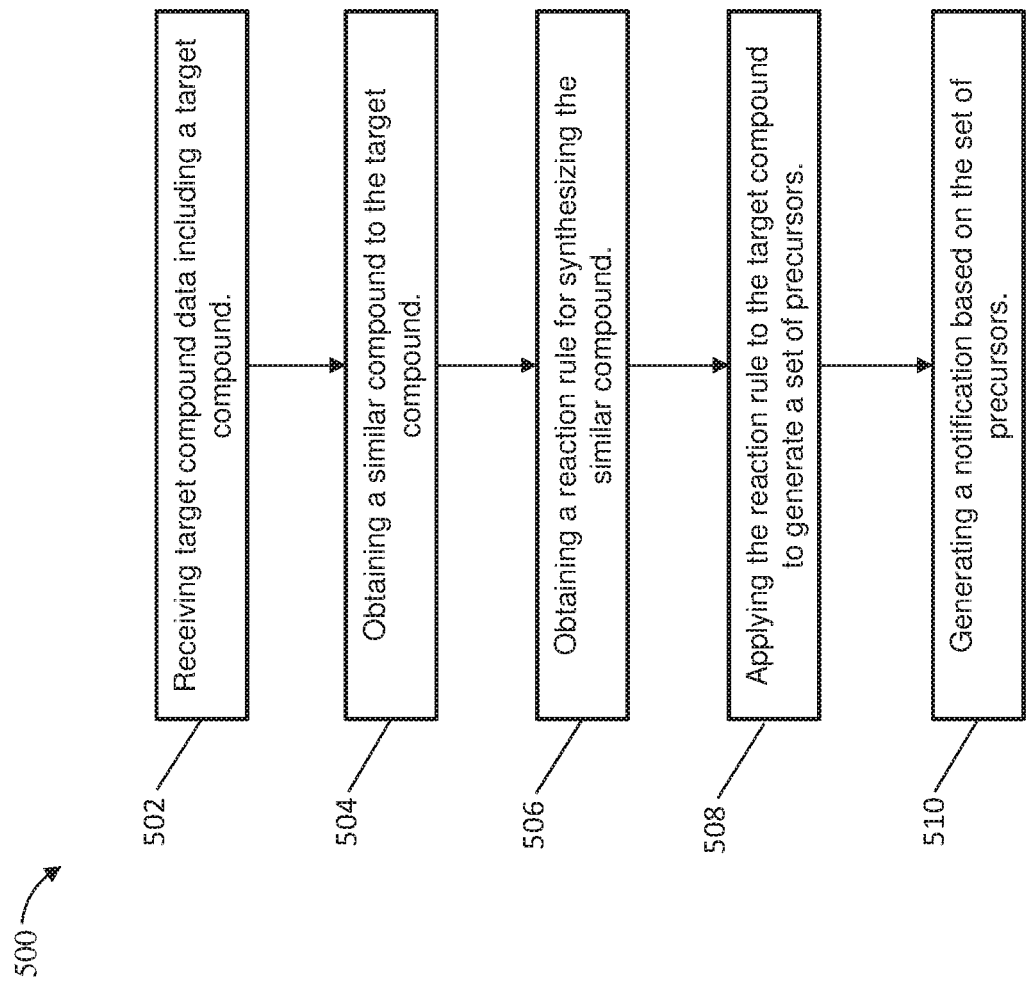
FIG. 5 depicts a flow diagram of a method for determining whether a target compound can be synthesized using known pathways for similar compounds according to one or more embodiments of the present invention.

FIG. 5 illustrates a flow diagram of a method 500 for determining whether a target compound can be synthesized using known pathways for similar compounds according to one or more embodiments. As shown at block 502, target compound data 404 is received (e.g., by the pathway construction module 402), according to one or more embodiments.

As shown at block 504, the pathway construction module 402 obtains a similar compound (i.e., a compound similar to the target compound according to one or more embodiments). In some embodiments, the pathway construction module 402 obtains the similar compound in response to receiving the target compound data 404.

The pathway construction module 402, as shown at block 506, obtains from the compound and pathway database 406 a reaction rule for synthesizing the similar compound, according to one or more embodiments. As shown at block 508, the pathway construction module 402 applies the reaction rule to the target compound to generate a set of precursors, according to one or more embodiments. In some embodiments, the pathway construction module 402 determines whether the reaction rule is valid as applied to the target compound.

As shown at block 510, pathway notification module 410 generates a notification based on the set of precursors, according to one or more embodiments. In some embodiments, the notification is provided to a user of the pathway construction module 402. In some embodiments, the notification is provided to a client system, according to one or more embodiments. The notification can include, for example, a complete pathway (i.e., series of reaction rules) for synthesizing the target compound from starting materials.

Additional processes also can be included, and it should be understood that the processes depicted in FIG. 5 represent illustrations, and that other processes can be added or existing processes can be removed, modified, or rearranged without departing from the scope and spirit of the present invention.

The present techniques can be implemented as a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry and to perform aspects of the present invention.

Aspects of the present invention are described herein with reference to flowchart illustrations and/or block diagrams of methods, apparatus (systems), and computer program products according to aspects of the present invention. It is understood that each block of the flowchart illustrations and/or block diagrams, and combinations of blocks in the flowchart illustrations and/or block diagrams, can be implemented by computer readable program instructions.

These computer readable program instructions can be provided to a processor of a special purpose computer or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the present invention. In this regard, each block in the flowchart or block diagrams can represent a module, segment, or portion of instructions, which includes one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It is understood that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments described herein.

What is claimed is:

1. A computer-implemented method for determining whether a target compound can be synthesized using known pathways for similar compounds, the method comprising:
 receiving, by a processor, target compound data comprising a target compound having an unknown synthesis;
 obtaining, by the processor, a similar compound to the target compound, the similar compound having a known synthesis;
 obtaining, by the processor, a reaction rule for synthesizing the similar compound from a first set of precursors;
 determining, by the processor, that the reaction rule for synthesizing the similar compound results in a valid pathway for synthesizing the target compound;
 applying, by the processor, the reaction rule for synthesizing the similar compound to the target compound to generate a second set of precursors that, upon application of the reaction rule, synthesize the target compound, wherein the reaction rule generates different precursors when applied to the target compound than are generated when the same reaction rule is applied to the similar compound; and
generating, by the processor, a notification comprising the second set of precursors.

2. The computer-implemented method of claim 1, wherein obtaining the similar compound further comprises retrieving, by the processor, the similar compound from a database comprising a plurality of compounds.

3. The computer-implemented method of claim 2, wherein the database further comprises a plurality of reaction rules associated with one or more compounds stored in the database and a set of infeasible compounds for which no reaction rules are available.

4. The computer-implemented method of claim 1, wherein obtaining, by the processor, a similar compound further comprises:
calculating, by the processor, a similarity score between the target compound and a compound stored in a database;
comparing, by the processor, the similarity score to a threshold; and
in response to determining that the threshold is satisfied, obtaining, by the processor, the compound from the database.

5. The computer-implemented method of claim 4, wherein calculating, by the processor, the similarity score further comprises calculating a Jaccard coefficient.

6. The computer-implemented method of claim 1, wherein the target compound data further comprises a compound name, a chemical structure, or a molecular fingerprint.

7. The computer-implemented method of claim 6, wherein the molecular fingerprint comprises bit strings that encode a presence or an absence of a functional group.

8. The computer-implemented method of claim 1, further comprising:
determining, by the processor, a similar precursor compound to a precursor in the set of precursors;
obtaining, by the processor, a precursor reaction rule for synthesizing the similar precursor compound;
applying, by the processor, the precursor reaction rule to the precursor to generate one or more precursors; and
including, by the processor, the one or more precursors in the set of precursors.

9. A system for determining whether a target compound can be synthesized using known pathways for similar compounds, the system comprising:
a memory having computer readable instructions; and
a processing device for executing the computer readable instructions, the computer readable instructions cause the processing device to:
receive target compound data comprising a target compound having an unknown synthesis;
obtain a similar compound to the target compound, the similar compound having a known synthesis;
obtain a reaction rule for synthesizing the similar compound from a first set of precursors;
determine that the reaction rule for synthesizing the similar compound results in a valid pathway for synthesizing the target compound;
apply the reaction rule for synthesizing the similar compound to the target compound to generate a second set of precursors that, upon application of the reaction rule, synthesize the target compound, wherein the reaction rule generates different precursors when applied to the target compound than are generated when the same reaction rule is applied to the similar compound; and
generate a notification comprising the second set of precursors.

10. The system of claim 9, wherein obtaining the similar compound further comprises obtaining the similar compound from a database comprising a plurality of compounds.

11. The system of claim 10, wherein the database further comprises a plurality of reaction rules associated with one or more compounds stored in the database and a set of infeasible compounds for which no reaction rules are available.

12. The system of claim 9, wherein the computer readable instructions further cause the processing device to:
calculate a similarity score between the target compound and a compound stored in a database;
compare the similarity score to a threshold; and
in response to determining that the threshold is satisfied, obtain the compound from the database.

13. The system of claim 12, wherein calculating the similarity score further comprises calculating a Jaccard coefficient.

14. The system of claim 9, wherein the target compound data further comprises a compound name, a chemical structure, or a molecular fingerprint.

15. The system of claim 14, wherein the molecular fingerprint comprises bit strings that encode a presence or an absence of a functional group.

16. The system of claim 9, wherein the computer readable instructions further cause the processing device to:
determine a similar precursor compound to a precursor in the set of precursors;
obtain a precursor reaction rule for synthesizing the similar precursor compound;
apply the precursor reaction rule to the precursor to generate one or more precursors; and
include the one or more precursors in the set of precursors.

17. A computer program product for determining whether a target compound can be synthesized using known pathways for similar compounds, the computer program product comprising:
a computer readable storage medium having program instructions embodied therewith, the program instructions executable by a processing device to cause the processing device to perform a method comprising:
receiving target compound data comprising a target compound having an unknown synthesis;
obtaining a similar compound to the target compound, the similar compound having a known synthesis;
obtaining a reaction rule for synthesizing the similar compound from a first set of precursors;
determining that the reaction rule for synthesizing the similar compound results in a valid pathway for synthesizing the target compound;
applying the reaction rule for synthesizing the similar compound to the target compound to generate a second set of precursors that, upon application of the reaction rule, synthesize the target compound, wherein the reaction rule generates different precursors when applied to the target compound than are generated when the same reaction rule is applied to the similar compound; and
generating a notification comprising the second set of precursors.

18. The computer program product of claim 17, wherein obtaining the similar compound further comprises retrieving the similar compound from a database comprising a plurality of compounds.

19. The computer program product of claim 18, wherein the database further comprises a plurality of reaction rules associated with one or more compounds stored in the database and a set of infeasible compounds for which no reaction rules are available.

20. The computer program product of claim 19, wherein obtaining a similar compound further comprises:
- calculating a similarity score between the target compound and a compound stored in a database;
- comparing the similarity score to a threshold; and
- in response to determining that the threshold is satisfied, obtaining the compound from the database.

* * * * *